United States Patent [19]

Hillberry et al.

[11] 4,216,549
[45] Aug. 12, 1980

[54] SEMI-STABLE TOTAL KNEE PROSTHESIS

[75] Inventors: Benny M. Hillberry, West Lafayette; Donald B. Kettelkamp, Carmel, both of Ind.

[73] Assignee: Purdue Research Foundation, West Lafayette, Ind.

[21] Appl. No.: 864,616

[22] Filed: Dec. 27, 1977

Related U.S. Application Data

[63] Continuation-in-part of Ser. No. 802,780, Jun. 2, 1977, abandoned.

[51] Int. Cl.² ............................................. A61F 1/24
[52] U.S. Cl. .................................. 3/1.911; 128/92 C
[58] Field of Search ................ 3/1.911, 1.91, 1.9, 3/1; 128/92 C

[56] References Cited

U.S. PATENT DOCUMENTS

| | | | |
|---|---|---|---|
| 3,728,742 | 4/1973 | Averill et al. | 3/1.911 |
| 3,869,729 | 3/1975 | Attenborough | 3/1.91 |
| 3,869,731 | 3/1975 | Waugh et al. | 3/1.911 |

FOREIGN PATENT DOCUMENTS

| | | | |
|---|---|---|---|
| 2545821 | 4/1976 | Fed. Rep. of Germany | 3/1.911 |
| 2550704 | 5/1976 | Fed. Rep. of Germany | 3/1.911 |

*Primary Examiner*—Ronald L. Frinks
*Attorney, Agent, or Firm*—John R. Nesbitt

[57] ABSTRACT

A three piece prosthetic knee joint comprised of a femoral component in the form of a shell member having convex condylar portions with an insert having a top surface with concave portions which receive said condylar portions of the femoral component and a bottom surface that rotatably engages a platform load bearing tibial component. The device may also include a cam mechanism between the insert and the tibial component so that lateral motion therebetween lifts the tibia thereby more nearly simulating natural knee joint action than can be obtained by existing two component prosthetic knee joints.

The present design is also adapted to provide a total knee joint replacement system whereby a single surgical technique may be employed, and then the correct components may be inserted according to the observed condition of the knee.

7 Claims, 10 Drawing Figures

SEMI-STABLE TOTAL KNEE PROSTHESIS

RELATED APPLICATION

This application is a continuation-in-part of our co-pending U.S. patent application, Ser. No. 802,780, filed June 2, 1977, and entitled "Semi-Stable Total Knee Prosthesis" now abandoned.

BACKGROUND OF THE INVENTION

The success of the total hip replacement in recent years has prompted considerable interest in the development of total joint replacement for several other anatomical joints. The success of the total joint replacements is largely due to the materials being used; polymethylmethacrylate ("bone cement"), high density polyethylene and a suitable corrosion resistant metal. With the knee, however, several problems have been encountered. These problems, caused primarily by the severe loading conditions within the knee joint, have led to many different prosthesis designs, none of which appear to be entirely satisfactory.

There are basically two types of knee prostheses: The earlier hinge or pin type, illustrated, for example by U.S. Pat. No. 3,696,446 issued to Bousquet, et al, and the more recent condylar replacement type, illustrated by U.S. Pat. No. 3,816,855 issued to Saleh. The lack of rotation about the axis of the tibia in the hinge prosthesis may result in loosening of one of the components. This combined with pin wear and the excessive bone removal required has resulted in limited use of the hinge type prosthesis.

Among the more severe porblems with condylar replacement prostheses of the Saleh type are loosening of the tibial components at the bone-cement interface and bone resorption, and plastic deformation ("plastic flow") of the high density polyethylene due to the high stresses and dislocation of the joint. In addition, it is not understood what effect the functional behavior of the prosthesis itself has on the overall performance of the patient with the implanted device. Nearly all of the condylar replacement prosthesis designs have a metal femoral component shaped similar to the anatomical condyles and a polyethylene tibial component either flat or grooved to provide a track for the femoral "condyle."

SUMMARY OF THE INVENTION

The present invention consists of three components, a femoral component and a tibial component with an insert component between these two. This insert "floats" between the femoral and tibial components, but also provides desired constraint in certain directions.

Flexion of the knee joint is permitted by a spherical condyle shape on the femoral component which rotates on a concentric surface of the insert component. The contact area of the insert is made as large as possible. The condyles in the femoral component are spherical surfaces which permit front to rear rotation and sideways rotation which allow an excessive lateral force to be carried by the collateral ligaments and other ligamentous structure.

The interface between the insert and the tibial component includes a pair of substantially flat engaging faces and a "pin" or protrusion from either the tibial component or the insert component which extends into a cavity or bore in the other thereby allowing rotation of the tibia about its axis while providing frontal and lateral constraint. Centrally located cooperating cam surfaces can provide a camming action when the tibia is rotated and/or shifted from side to side. A displacement results along the axis of the tibia thereby providing increased stability by tightening the ligaments.

With the present design, the center of rotation for flexion and for tibial rotation are located to closely duplicate the actual motion of the knee. This is important in obtaining proper function of the implanted prosthesis. Loosening tendencies of the tibial component are significantly reduced compared with condylar replacement type knee joints because the instant tibial component is made of metal (loosening of metal femoral components has generally not been a problem with existing designs). The contact areas of the sliding surfaces are as large as possible to reduce the stresses.

Another important feature of this design is that any excessive wear normally occurs on the insert component, and this component can be readily replaced since it is not permanently attached to either of the other components nor the bone.

Another advantage of the three component system is that it meets all the requirements inherent in the various degrees of deterioration of the knee joint. The basic differences that affect the choice of components used in a given patient depend upon the degree of stability of prosthesis desired. The surgical implant procedures will be similar for all types of knees. Component choices are provided for "good" knees, namely those having both good cruciate and collateral ligaments. Separate components are provided for knees having these ligaments in deteriorated condition.

THE DRAWINGS

DETAILED DESCRIPTION OF THE INVENTION

Figure 1:
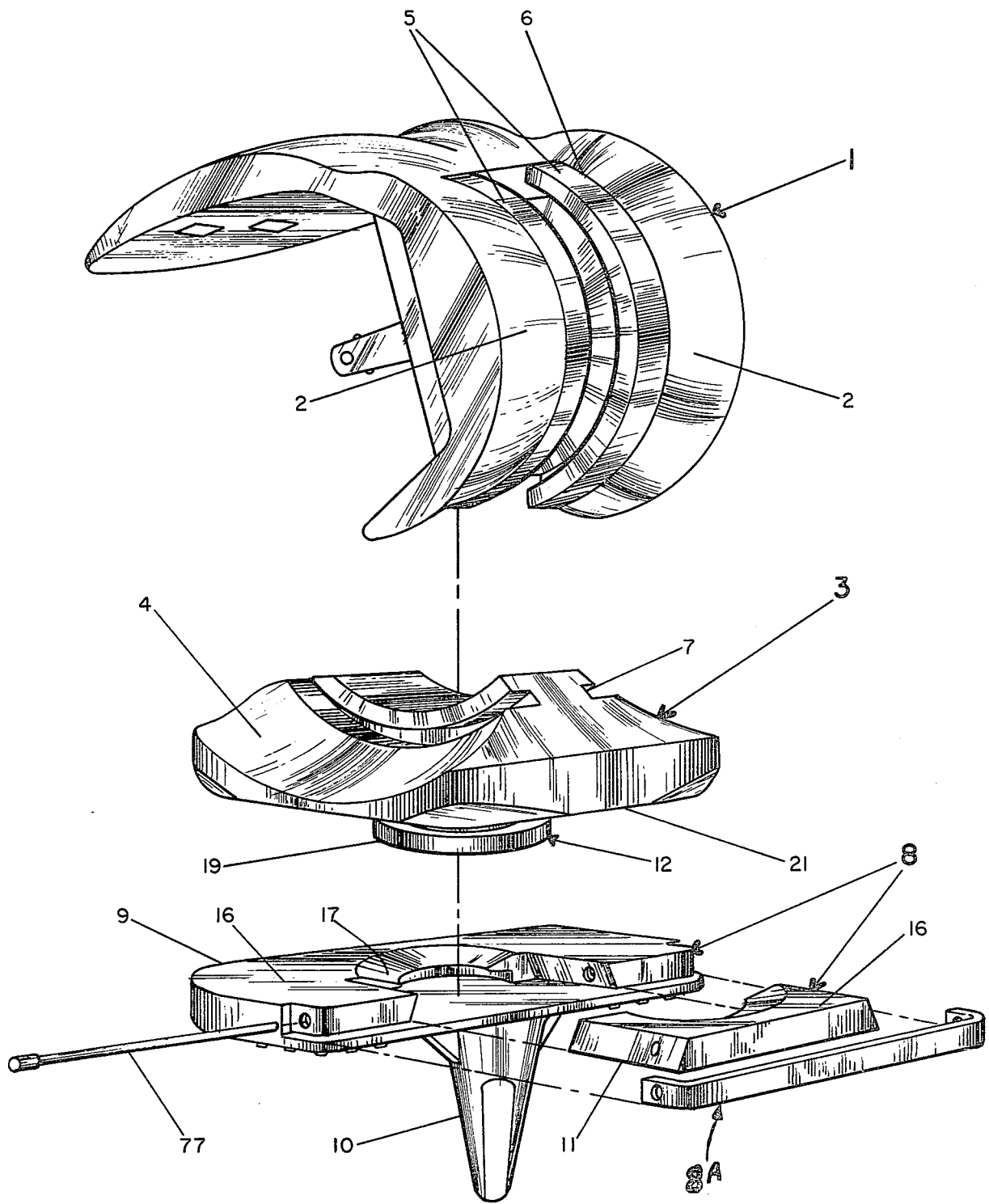
FIG. 1 is an exploded perspective view of the components of one embodiment of the present invention for use with a knee having both inadequate collateral and cruciate ligaments.
Figure 2:
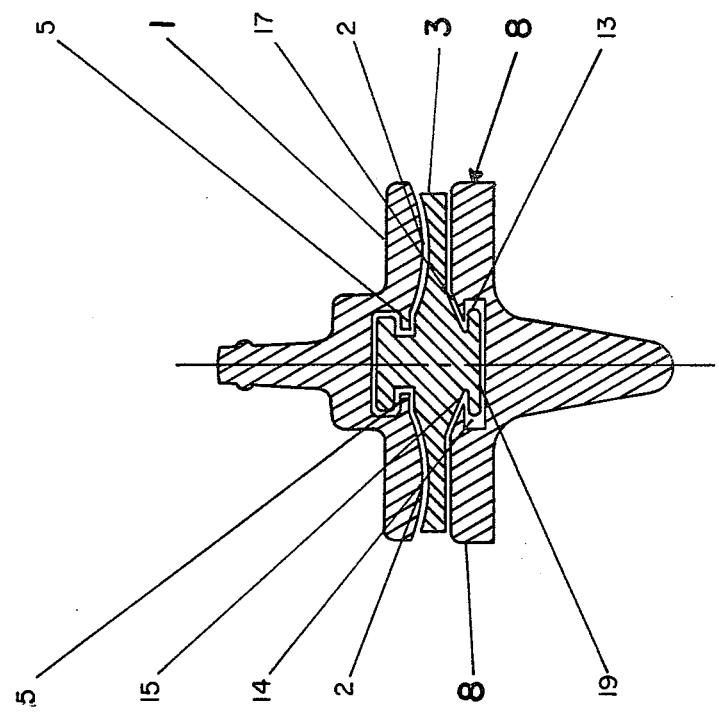
FIG. 2 is a cross section of the device of FIG. 1 in an assembled condition.

The embodiment of the present invention as shown in FIGS. 1 and 2 is comprised of a femoral component 1, having an overall shell type configuration as is common for prosthetic knee joints of the so-called condylar replacement type. Component 1 has a pair of convex portions 2 adapted to be received on concave surfaces 4 of the insert component 3. Flanges or ribs 5 protrude from the interior edges 6 of the femoral component, such flanges being sized and located for loose slidable engagement with guideways or grooves 7 formed in the insert component 3.

The femoral component 1 is preferably made of metal, the insert component 3 is perferably made of a high density polyethylene material, and the tibial component 8 is made in two parts that are preferably formed of metal. For ease of construction, an additional lock bar 8A may be provided, so that lock portion 11, of element 8, may be captured between 8A and bearing plate portion 9 by means of a pin 77, or other fastener.

The tibial component 8 includes a bearing plate portion 9 which includes load bearing surfaces 16 for engaging load transmission plate 21 on the bottom surface of component 8. Tibial component 8 includes a vane 10 adapted for permanent adhesion to the tibia, and said tibial component also includes a locking portion 11 which, when secured in place, captures the enlarged lower portion 13 of downwardly depending cylindrical protuberance 12 of insert component 3.

Protuberance 12 is cylindrical and includes a load transmission plate 19, and protuberance 12 may also have an enlarged bevelled surface 15 at its top end.

The enlarged lower portion 13 of protuberance 12 is received in chamber 14 of tibial component 8 in mutually rotatable relationship and annular cam surface 17 is formed in the top surface 16 of component 8 adjacent chamber 14. Locking portion 11 of tibial component 8 is then secured by screws 77, or a pin arrangement, or other fastening means, to bearing plate portion 9 of component 8.

The ribs 5 of component 1 have a thickness appreciably less than grooves 7, and the enlarged lower portion 13 of protuberance 12 has a thickness appreciably less than chamber 14 of component 8, as may be readily seen in FIG. 2. These "sloppy" sizings allow a certain amount of movement of the insert compoment 3 between the femoral and tibial components.

When the tibia is moved from side to side the bevelled surface 15 tends to slide upward on annular cam surface 17 thereby permitting desirable axial displacement of the tibia while providing both frontal and lateral constraints at the same time. This type of displacement is unique in prosthetic knee joints.

Figure 4:
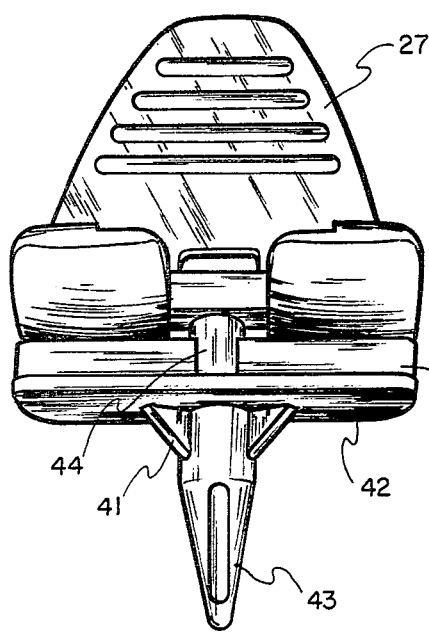
FIG. 4 is a front prospective view of a second, and now preferred, embodiment of this invention.
Figure 5:
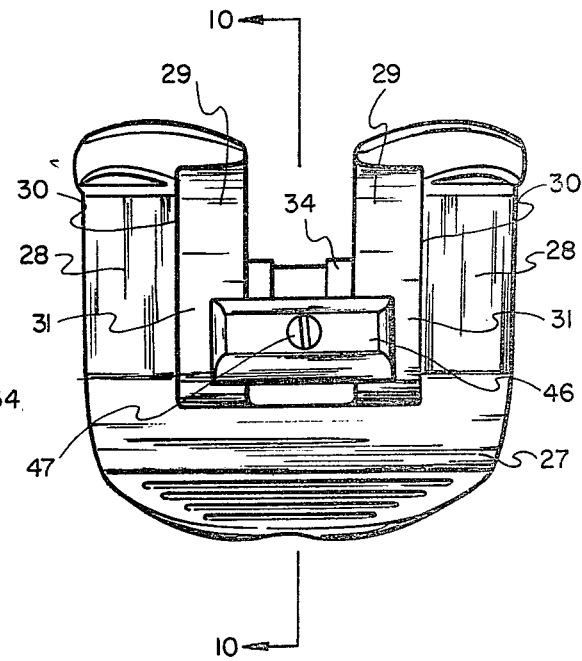
FIG. 5 is a top view of the embodiment of this invention as shown in FIG. 4.
Figure 6:
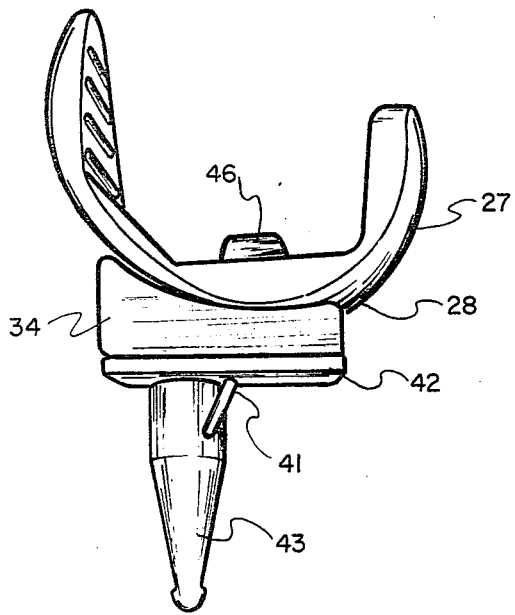
FIG. 6 is a side view of the embodiment of this invention as shown in FIG. 4.

The second embodiment of the present invention is shown in FIGS. 4 through 10 to include a femoral component 27 similar to that shown in FIG. 1. As best shown in FIGS. 4 and 6, femoral component 27 has an overall shell type configuration, as is common for prosthetic knee joints of the so-called condylar replacement type. Component 27 includes a pair of convex portions 28 and a pair of inwardly directed flanges or rib 29 extending form opposite interim edges 30 and having upper surfaces 31, with the outer edges of the ribs terminating adjacent to one another to form a notch therebetween.

Figure 7:
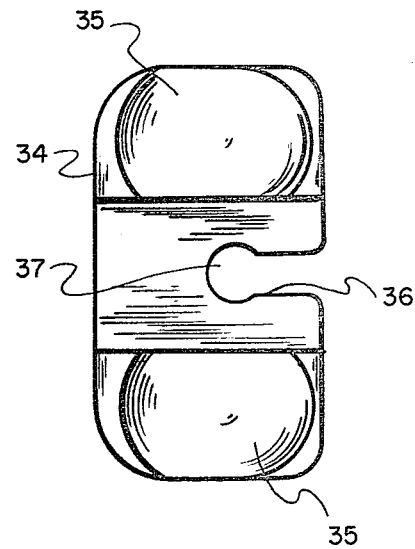
FIG. 7 is a top view of the insert component shown in FIGS. 4 through 6.

Insert component 34, like component 3, is perferably made of high density polyethylene material, and, as best shown in FIG. 7, includes a pair of concave surfaces 35 that engage the convex portions 28 of femoral component 27 when the unit is assembled as shown in FIGS. 4, 5, 6, and 10. In addition, a notch, or aperture, 36 in insert component 34 terminates in the central portion of the insert component in an enlarged passage 37 through the insert component.

Figure 8:
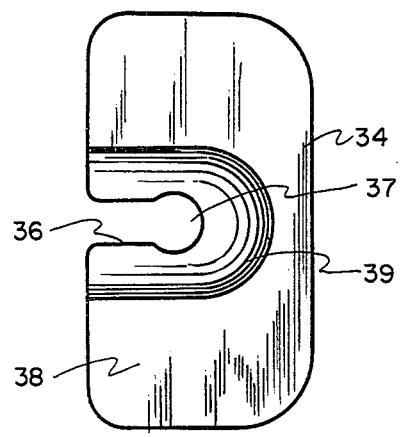
FIG. 8 is a bottom view of the insert component shown in FIGS. 4 through 6.

The substantially flat bottom portion 38 of the insert component provides a load transmission plate, and, as can best be seen in FIG. 8, inwardly tapered side walls 39 provide a cam surface adjacent to passage 37.

Figure 9:
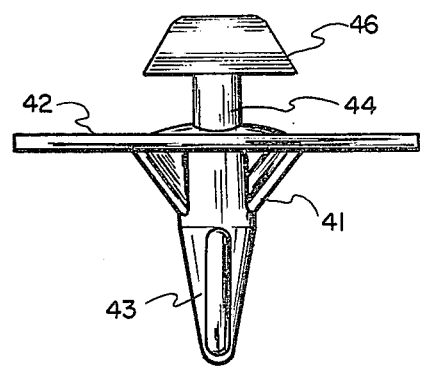
FIG. 9 is a side view of the tibial component shown in FIGS. 4 through 6.

Tibial component 41 is shown alone in FIG. 9 and in the assembled unit in FIGS. 4, 5, 6, and 10. Tibial component 41, like femoral component 27, is preferably made of metal, and has an upper surface 42 that functions as a load bearing plate portion and engages load transmission plate 21 of insert component 34 when the unit is assembled. Tibial component 41 also includes a downwardly extending vane 43 adapted for permanent adhesion to the tibia.

A post 44 extends outwardly from upper surface 42 of tibial component 41. As shown in the drawings, post 44 is received in and extends through passage 37 in insert component 34 when the unit is assembled so that the outer end of the post passes through the notch formed by ribs 29 of femoral component 27.

Figure 10:
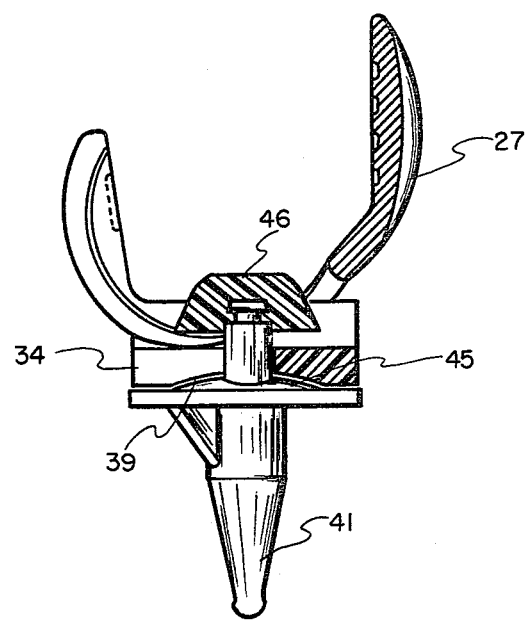
FIG. 10 is a cross-section taken through lines 10—10 of FIG. 5.

As can best be seen in FIG. 9, a cylindrical cam surface 45 extends upwardly and outwardly from the upper surface 42 of tibial component 41 adjacent to post 44. As shown, this cam surface mates with cam surface 39 of insert component 34 when the unit is assembled as shown in FIG. 10.

A connector, or knob, 46 is positioned at the end of post 44, and this knob could be integrally formed with the post or removably secured thereto by means of a bolt 47 or other conventional fastening means, as indicated in FIG. 5.

The embodiment of the invention as shown in FIGS. 4 through 10 thus maintains the same general configuration of the embodiment of the invention as shown in FIGS. 1 and 2, and operates in the same general manner as described with respect thereto utilizing the same three components.

In the embodiment of the invention as shown in FIGS. 4 through 10, however, displacement limiting is accomplished in a different manner. As brought out hereinabove, the tibial component has a post extending upwardly through the passage in the insert component and through the notch in the femoral component, and terminates in a connector that is preferably of plastic molded to the top of the post with the connector engaging the upper surfaces 31 of ribs 29 when the unit is assembled to thereafter prevent vertical displacement of the unit.

In addition, the post is surrounded by a cam section that is tapered down to the load bearing surface 42 of the tibial component. This tapered area helps center the insert component that is in contact with the tibial component when the unit is assembled, and maintains the centering of the insert component to provide an energy absorbing capability for the device (this capability being also present in the embodiment of the invention shown in FIGS. 1 and 2).

For assembly of the embodiment of the invention shown in FIGS. 4 through 10, the notch in the insert component allows the post of the tibial component to be inserted into the passage in the insert component. The tibial and femoral components are normally attached to the bones with the insert component then being slid in between the other two components and snapped over the post. Should excessive wear or deformation later occur, the plastic insert component can thus be easily removed and another inserted.

Figure 3:
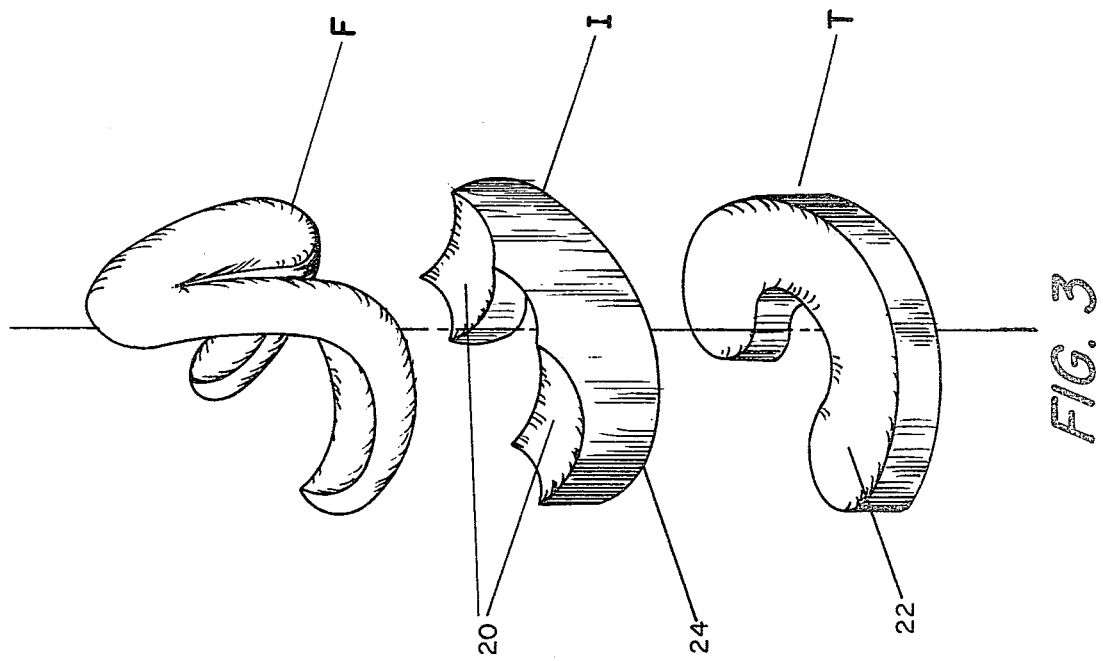
FIG. 3 is a diagrammatic representation of the three components of the invention used for a knee having both good cruciate and collateral ligaments.

The embodiments described above are especially adapted for knees in which both the cruciate and collateral ligaments are inadequate. However, by use of different types of insert components and different types of tibial components, knees of all conditions may be successfully surgically implanted with a three component joint according to the present invention. FIG. 3 illustrates inserts that may be used with "good" knees (cruciate and collaterals in good shape). The femoral component denoted as F is for use with "good" knees. Component I has a laterally dished top surface 20 shich also has a concave configuration adapted for rotatable engagement with F, and the tibial component T has a concave top surface 22 which engages the concave bottom surface 24 of I. In a "good" knee, the healthy ligaments hold the three elements in slidable engagement and no flanges, guideways and the like are needed.

It will appreciated that by use of the total component system described, substantially the same surgical techniques may be employed in repairing all manner and condition of knees.

What is claimed is:

1. A prosthetic knee joint comprising:
   two pairs of coacting male and female load bearing condylar elements, one of said pairs being carried by a first component,
   another of said pairs being carried by a second component;
   the male elements each including a spheroidal protuberance and an arcuate rib;
   the female elements each including a spheroidal socket adapted to coact with the correspondingly shaped male component, and each female element also including an arcuate groove adapted to receive said arcuate rib so that front to back rotational motion is permitted between the male elements and the female elements but front to back linear motion and side to side rotatable motion therebetween is substantially constrained;
   said second component including a flat load transmission plate;
   a third component including platform load bearing means adapted to support the load transmission plate of said second component;
   said third component also including connection means adapted to engage said second component so that rotation therebetween in a direction about the normal axis of an extended leg is permitted.

2. The knee joint according to claim 1 in which the said second component includes a downwardly depending cylindrical protruberance and the said third component includes a cylindrical chamber sized to loosely receive said cylindrical protuberance, said cylindrical chamber including an enlarged cylindrical portion adjacent its bottom, and said cylindrical protuberance of the second component including an enlarged lower end having a diameter greater than that of the top portion of said cylindrical chamber whereby, upon assembly of the second component to the third component, the two components are captured with respect to one another while rotation between the two is not constrained.

3. The knee joint according to claim 2 in which an annular surface is bevelled on the load bearing top surface of the third component adjacent the top end of said cylindrical chamber;
   and said downwardly depending cylindrical protuberance including an enlarged bevelled surface at its top end;
   the lower end of said chamber having a larger diameter than the enlarged lower end of said protuberance with the diameter differential being sufficient to permit limited lateral shifting of the second component with respect to the third component;
   the said bevelled surface being sized to provide a camming action when the second component is moved transversely respecting the third component whereby a lifting action is provided along the longitudinal axis of a normally extended leg.

4. A prosthetic knee joint, comprising:
   a femoral component having a pair of spaced convex surface portions with flanges extending inwardly thereupon and terminating adjacent to each other to form a notch therebetween extending parallel to and between said convex surfaces, said femoral component being adapted for permanent adhesion to a femur;
   an insert component having a pair of spaced surface portions complementary to and engaging said convex surface portions of said femoral component, said insert component having a slot in one side thereof with said slot terminating in an enlarged bore in the central portion of said insert component between said concave surface portions, said insert component also having a load bearing surface portion at the side of said insert component opposite to that of said concave surface portions with said bore extending from said load bearing surface and having a tapered opening thereat defining a cam surface; and
   a tibial component adapted for permanent adhesion to a tibia and having a load bearing surface portion engaging said load bearing surface portion of said insert component, said tibial component also having a post extending from said load bearing portion through said bore in said insert component and through said notch in said femoral component, said post terminating in an enlarged head portion engaging said flanges of said femoral component at the side of said flanges opposite to that of said insert component, and said load bearing portion adjacent to said post being an upstanding cylindrical cam surface complementary to that of said insert component and in engagement therewith.

5. The knee joint of claim 4 in which said insert component is most susceptible to wear and may be replaced by another insert component that is assembled by passing said post through said slot to the bore of said insert component.

6. A prosthetic knee joint comprising:
   a femoral component adapted for permanent adhesion to a femur and including a pair of spaced, substantially parallel convex portions having ribs therebetween which form a notch;
   an insert component including a pair of concave portions which are substantially complementary with the convex portions of said femoral component and each of which engages a different one of said convex portions of said femoral component, said pair of concave portions having a body portion therebetween with passage means being formed therethrough;
   a tibial component adapted for load bearing and adapted for permanent adhesion to a tibia, said tibial component including connecting means extending therefrom through said passage means and said notch with such connecting means of said tibial component including a post extending through said passage means and said notch, with said post having an enlarged element at the free end thereof engageable with said ribs at the sides thereof opposite to that of said insert component.

7. A prosthetic knee joint comprising:
a femoral component adapted for permanent adhesion to a femur, and including a convex portion;
a tibial component adapted for load bearing and adapted for permanent adhesion to a tibia, said tibial component including an outwardly and upwardly tapered cylindrical cam surface;
an insert component including a concave portion which is substantially complementary with the said convex portion of said femoral component and adapted for movable engagement with respect thereto with said insert also including a load transmission portion which both bears on said tibial component and is rotatable with respect thereto, and further including a cam surface which is an inwardly and upwardly at least partially cylindrical tapered surface of substantially the same diameter as that of said cam surface of said tibial component.

* * * * *